United States Patent [19]
van Lierde

[11] Patent Number: 5,601,098
[45] Date of Patent: Feb. 11, 1997

[54] METHOD AND APPARATUS FOR APPLYING METHOPRENE TO ORIENTAL TOBACCO

[75] Inventor: Herman van Lierde, Izmir, Turkey

[73] Assignee: Dimon Incorporated, Danville, Va.

[21] Appl. No.: 460,574

[22] Filed: Jun. 2, 1995

[51] Int. Cl.$^6$ ................................................ A24B 3/18
[52] U.S. Cl. ............................................ 131/300; 131/290
[58] Field of Search ........................... 131/290, 300, 131/296, 302, 304, 306; 426/335, 235, 286

[56] References Cited

U.S. PATENT DOCUMENTS

| | | | |
|---|---|---|---|
| 4,665,931 | 5/1987 | Prunerie et al. | 131/300 |
| 4,762,835 | 8/1988 | Whittle et al. | |
| 5,167,243 | 12/1992 | Cowan et al. | 131/296 X |
| 5,196,610 | 3/1993 | Bushell et al. | |
| 5,225,607 | 7/1993 | Bushell et al. | |
| 5,501,032 | 3/1996 | Pitman. | |

*Primary Examiner*—Jennifer Bahr

[57] ABSTRACT

A method and apparatus for applying liquid methoprene to oriental tobacco to inhibit the growth of tobacco beetles by which oriental tobacco leaves are subjected to kinetic energy of high-pressure dry steam exiting from nozzles against and through the tobacco leaves, and the liquid methoprene is injected into the steam before it exits the nozzles. The apparatus for applying the methoprene includes a vibrating steam tunnel having steam nozzles, a supply of liquid methoprene, and an injector for injecting the liquid methoprene into the steam. At least one such injector is provided in a manifold having a high pressure steam inlet and a plurality of outlets in fluid communication with the nozzles, respectively, the at least one injector being oriented to discharge in the direction of steam flow.

9 Claims, 3 Drawing Sheets

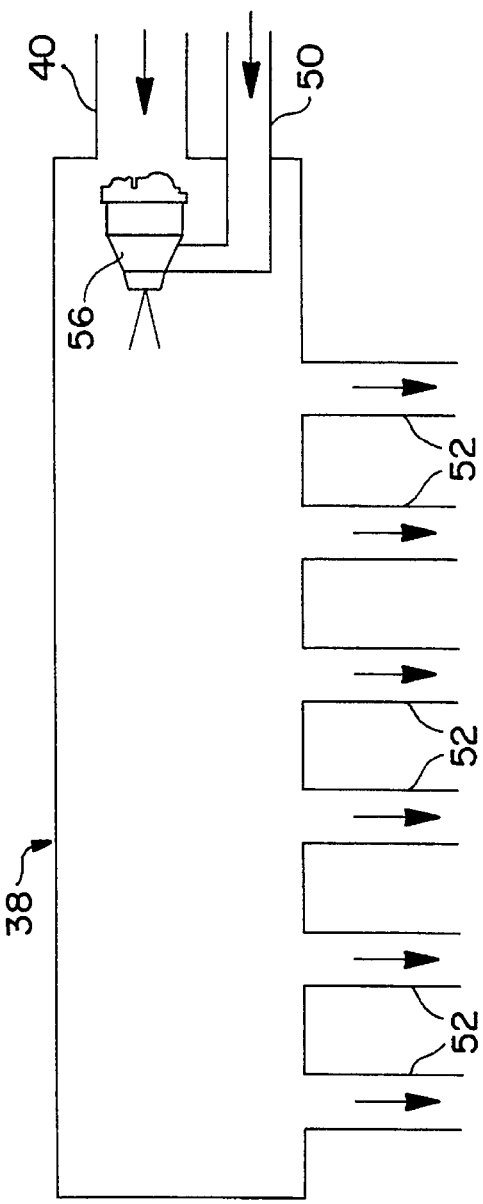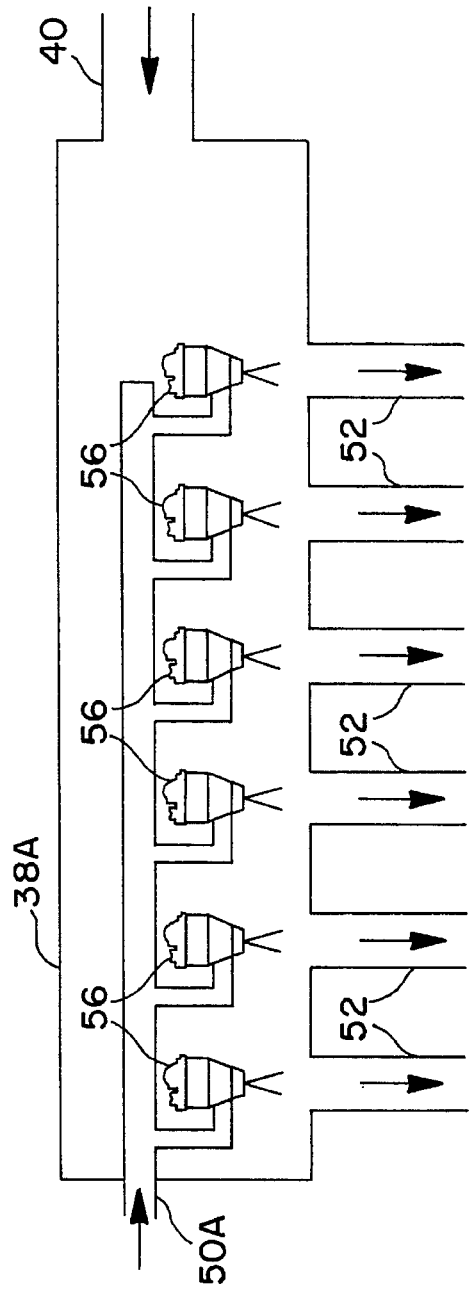

METHOD AND APPARATUS FOR APPLYING METHOPRENE TO ORIENTAL TOBACCO

BACKGROUND OF THE INVENTION

The present invention relates to a method and apparatus for treating tobacco, and, more particularly, to such a method and apparatus for applying a non-toxic tobacco beetle inhibitor to small leaf tobacco exemplified by oriental tobacco.

In tobacco processing, it is known to apply methoprene to the tobacco leaves as a larva growth inhibitor to eliminate the threat of beetle infestation in tobacco. Unlike conventional insecticides, (e.g., phostoxine, magnesium phosphide), which are highly toxic and have very short-term effects, methoprene is non-toxic, has a long lasting effect, and operates by interrupting the life cycle of cigarette beetles and other insects. Methoprene is commercially available in directly usable liquid form from Zoecon Corporation of Dallas, Tex. under the Registered Trademarks, "KABAT" and "DIANEX." Hereinafter, the term "liquid methoprene" will be used as a generic designation of these products of Zoecon Corporation and of other methoprene products in liquid form whether the product is a liquid phase, a liquid mixture, a liquid suspension or a liquid solution.

Liquid methoprene is applied on tobacco leaves during leaf processing using nozzles in a specified amount per unit volume of tobacco leaf to arrive at a spread of approximately 5 ppm of methoprene in the packed tobacco product. Therefore, it is important that the tobacco volume throughput per unit time is known at the point of application. In broad leaf tobacco production, liquid methoprene is applied after a redrying process, in which the redryer is preset to handle substantial volumes of tobacco per hour and with the leaves spread evenly over an apron conveyer. The latest liquid methoprene applying systems work with a weight slide connected to a solenoid cell which feeds information to a computer equipped to control a microflow pump. The computer calculates the tobacco throughout per minute and the microflow pump pumps a regulated amount of liquid methoprene through nozzles to be sprayed on the leaves.

However, in oriental tobacco leaf processing, redryers are not used and it is extremely difficult to measure throughput volume per unit time because of high fluctuation in volume throughout the processing system. The lay-out of traditional indigenous oriental tobacco processing factories makes it very expensive to use weight-belts, and measurements with photocells have been proven inaccurate because the high sand and dust content of oriental leaf tobacco distorts the light beams used with photocells.

Also, one of the main problems with the computer controlled system is that it is not adequately sensitive to measure small volume throughputs, which makes it of little or no use on smaller production lines typical of processing factories in the Mid-East. Another problem is the waste of liquid methoprene caused by a substantial turbulence in the open spraying cabin, resulting in an uncontrollable coverage of the tobacco leaf surface. Finally, the extremely dusty and sandy condition of oriental tobacco makes the process difficult to practice. The mechanism of the weight slide and solenoid cell system becomes clogged, and, because liquid methoprene is mixed with water at the end of the nozzles, a continuous buildup of mud around the nozzles occurs, and the mud eventually ends up in the product.

The computer controlled system is also expensive and, because of the high-tech design, it is difficult to calibrate and repair after a breakdown. All previously-mentioned problems with this form of application have also been reflected in laboratory analysis results, which show unsatisfactory coverage/spread of liquid methoprene in the finished product.

Oriental tobacco is characterized by its small leaf size, e.g., three to six inches in length. When stored for curing and later baled, the leaves agglomerate in "pads" which must be broken up or loosened into individual leaves for processing. Traditionally, mechanical leaf pad openers have been used to open the pads or to separate the leaves from each other. Such mechanical leaf pad openers use a beater, such as a revolving carousel of steel bars, to beat the pads physically until the leaves loosen up. These machines create an excessive amount of scrap because oriental leaf is not conditioned and tends to be very dry at the time of processing.

During the last few years, new developments in the processing of oriental tobacco have included the introduction of vibratory steaming tunnels. The tunnel solves the problems associated with mechanical leaf pad openers by using the kinetic energy in high-pressure, dry steam to condition the leaves and open the leaf pads, by development of extremely high turbulence in the closed environment of the tunnel. The system has been proven highly efficient in practice, and is gaining acceptance in factories which process oriental tobacco because of substantial reduction in scrap and the capability for obtaining a better end product with less leaf pads than previously possible.

One of the main requirements for the vibrating steam tunnel is an even flow of tobacco through the tunnel over steam nozzles. This is obtained by using a metering tube assisted with a volume backup system. Throughput volume is steady and the volume capacity of the tunnel is fixed according to the requirements of the processing system (e.g., 4 metric tons per hour).

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, the invention provides a method for applying liquid methoprene to oriental tobacco to inhibit the growth of tobacco beetles. The method comprises the steps of subjecting oriental tobacco leaves to kinetic energy of high-pressure dry steam exiting from nozzles against and through the tobacco leaves, and injecting the liquid methoprene into the steam before it exits through the nozzles. Preferably, the tobacco leaves subjected to the high pressure steam are fed at a constant rate of flow, and the injected liquid methoprene is metered in accordance with the constant rate of flow.

In another aspect, the invention provides an apparatus for applying methoprene to oriental tobacco, the apparatus comprising a vibrating steam tunnel having steam nozzles for subjecting oriental tobacco leaves to kinetic energy of high-pressure dry steam exiting from the nozzles against and through the tobacco leaves. Liquid methoprene from a supply is fed to injectors arranged in a conduit system for supplying steam to the nozzles.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIG. 5 is a schematic cross section showing one embodiment of a steam/methoprene feed manifold of the invention; and FIG. 6 is a schematic cross section showing an alternative manifold embodiment.

DESCRIPTION OF THE PREFERRED EMBODIMENT

Reference will now be made in detail to the present preferred exemplary embodiments of the invention, examples of which are illustrated in the accompanying drawings, Wherever possible, the same reference numbers will be used throughout the drawings to refer to the same or like parts.

In accordance with the invention, a system for applying liquid methoprene to oriental tobacco leaves is adapted to a conventional vibrating steam tunnel so that as the leaves are separated from multi-leaf pads in the tunnel by high pressure steam, the liquid methoprene is simultaneously applied to the leaves. Preferably, the liquid methoprene is injected into one or more conduits that supply steam to the tunnel.

Figure 1:
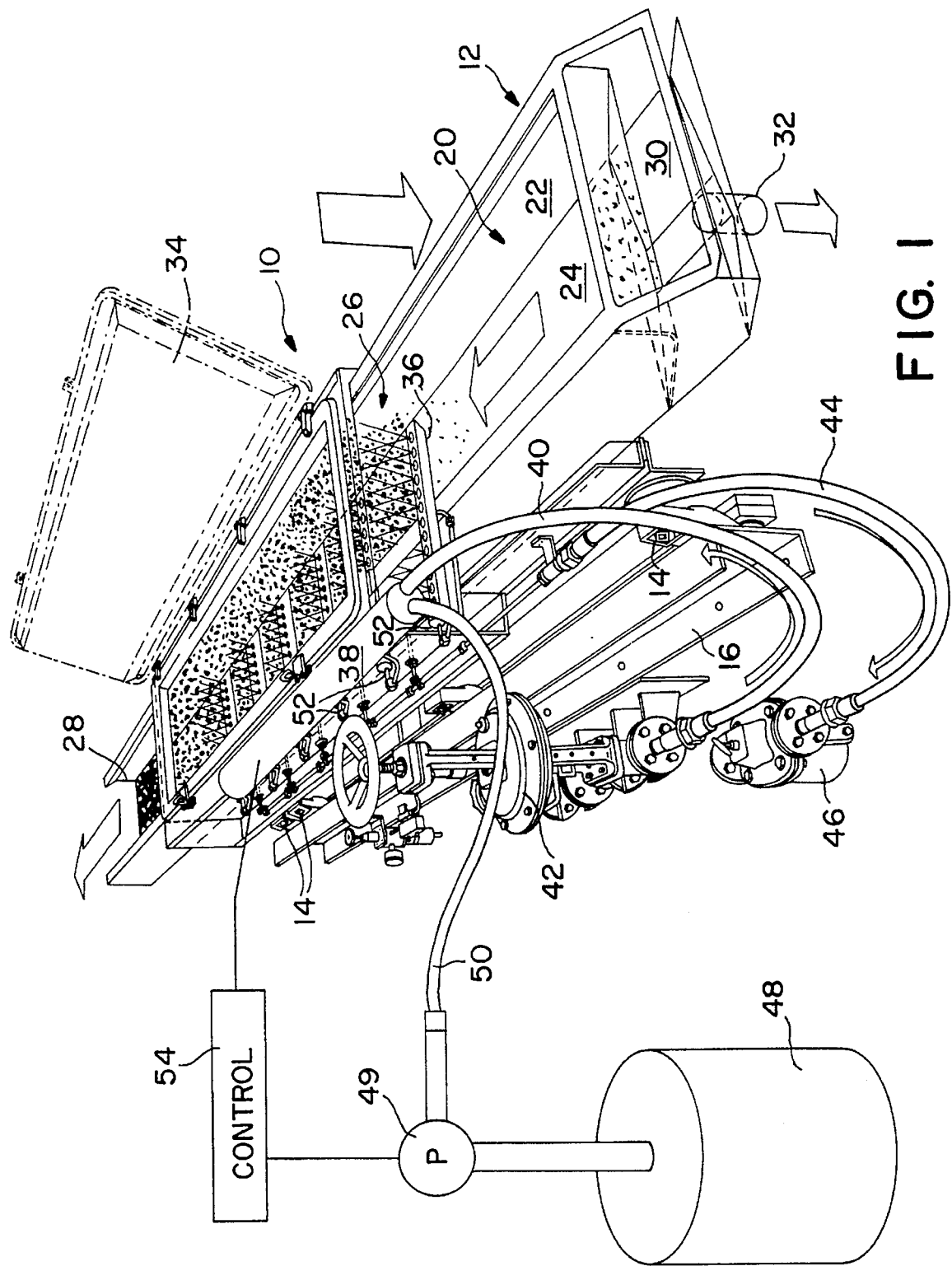
FIG. 1 is a partially schematic perspective view of the apparatus of the invention.

In FIG. 1 of the drawings, an embodiment of a vibrating steam tunnel equipped with the system of the present invention is shown and generally designated by the reference numeral 10. A vibrating steam tunnel available from Franz Sagemuller Gmbh was modified to achieve the depicted embodiment. The tunnel includes a elongated boxlike tray 12 supported by a plurality of rubber spring bumpers 14 on a pair of supporting side beams 16 (only one of which is shown in the perspective view of FIG. 1. Although not visible in the perspective of FIG. 1, a motor driven eccentric weight (not shown) supported by the bottom of the tray imparts low frequency vibrations to the tray. The vibrations, together with the design of the rubber spring bumpers, impart a horizontal feed to material contained in the tray 12. An electropneumatic control system 18 is associated with the tray 12.

The tray 12 has a feed hopper 20 at one end thereof and includes side walls 22 and a floor 24. The side walls 22 and floor 24 extend through a tunnel section 26, to be described in more detail below, to a discharge end 28. The floor 24 is elevated above an exterior tray bottom 30 having a dirt/water drainage port 32.

The tunnel section 26 is in the nature of an enclosure having a top cover 34 and has a plurality of laterally extending, longitudinally spaced elongated nozzles 36. The nozzles 36 discharge upwardly toward the door 34 after it is closed and through the material fed to the tray 12. The nozzles are connected with an input manifold 38 coupled by a feed hose 40 and an associated control valve 42.

The control valve 42 is supplied with dry steam under very high pressure so that the kinetic energy of the steam released from the nozzles 36 opens leaf pads, peculiar to oriental tobacco, to loosen the pads and separate the individual leaves thereof in an extremely highly turbulent atmosphere of steam in the relatively closed environment of the tunnel section 26. Steam condensate from the nozzle 36 is removed from through a condensate drainage conduit 44 to a condensate drain 46.

In the operation of vibrating steam tunnel 10, tobacco leaf pads are supplied to the feed hopper 20 at a constant volume per unit time by a metering tube (not shown). As the leaf pads enter the tunnel section 26, the pads are loosened and separated into individual tobacco leaves by the action of the dry steam discharge through the nozzle 36. As a result, the tobacco leaf flow toward the output end of the tunnel is steady and predictable.

In accordance with the present invention, the loosened and separated tobacco leaves in the tunnel section 26 are treated by application of liquid methoprene at a rate of application optimized for the rate of tobacco flow through the tunnel section 26.

In the illustrated embodiment, this application of liquid methoprene is accomplished by pumping liquid methoprene from a supply tank 48, using a pump 49, through a conduit 50 to one or more injectors located inside the manifold 38 and to be described in more detail below. As a result a mixture of liquid methoprene and steam is supplied to the nozzles by conduits 52 located between the manifold 38 and the nozzles 36. The rate of injection may be controlled accurately by a conventional controller 54.

In the operation of steam tunnel 10 to separate tobacco leaves from the agglomerated leaf pads, steam is introduced to the manifold 38 at a pressure approximating 10 atmospheres. In accordance with the invention, it is preferred that the liquid methoprene is introduced into the flow of steam to the nozzles 36 because the water molecules of the steam act as a carrier for the methoprene and facilitates travel of the methoprene through the system. To assure flow of the liquid methoprene from the supply 48 into the high pressure steam manifold 38, the pump 49 must be capable of developing pressure in excess of the 10 atmospheres of steam pressure.

Also, in accordance with the invention, it is preferred that the liquid methoprene be introduced to the steam through injectors of a class conventionally used as fuel injectors in internal combustion engines. Examples of such injectors are illustrated in FIGS. 2–4 of the drawings.

Figure 2:
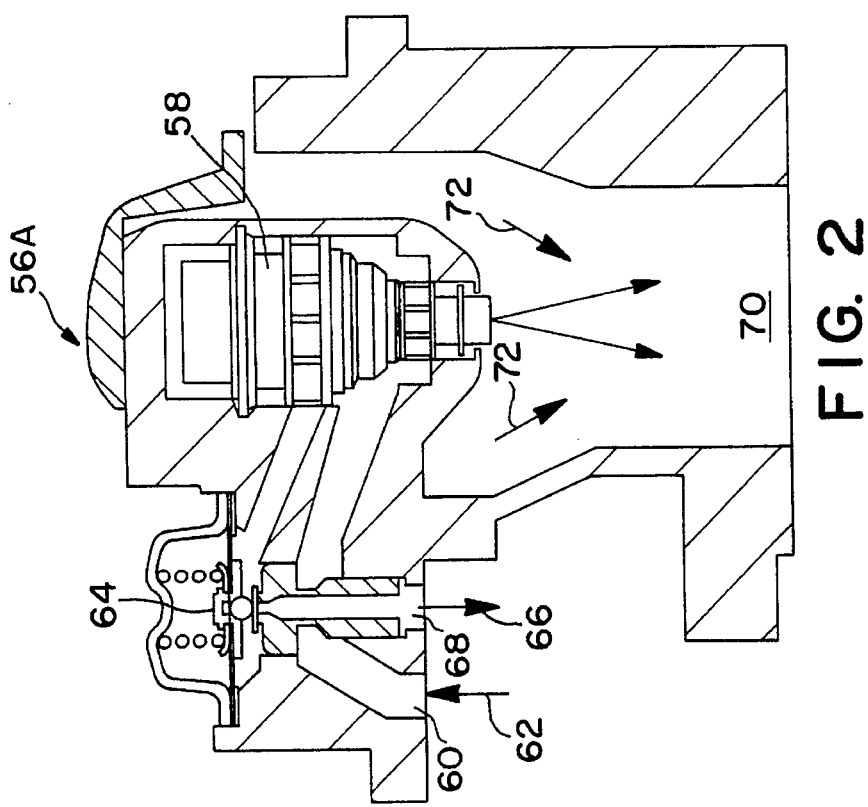
FIG. 2 is a largely schematic cross section illustrating one type of injector for metering liquid methoprene into high pressure steam.

In FIG. 2, a recycling-type fuel injector is generally designated by the reference numeral 56A and is of a construction similar, if not identical, to fuel injectors for diesel engines. In this type of injector, liquid methoprene is recycled past an injector unit 58 through a feed port 60 in the direction of the arrow 62. Pressure at the injector 58 is controlled by a pressure responsive valve 64 and excess liquid methoprene returned in a direction of the arrow 66 through an outlet or return port 68. An outlet 70 of the injector 56A is supplied with steam in the direction of the arrows 72. The injector unit 58 directs the liquid methoprene into the flow of steam represented by the arrows 72.

Figure 4:
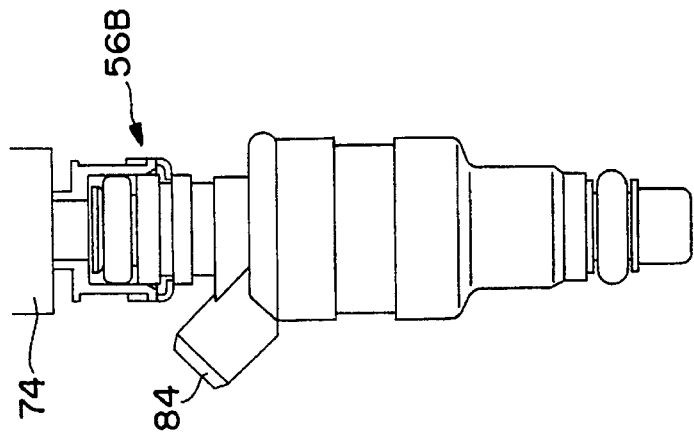
FIG. 4 is a side elevation of the injector shown in FIG. 3.
Figure 3:
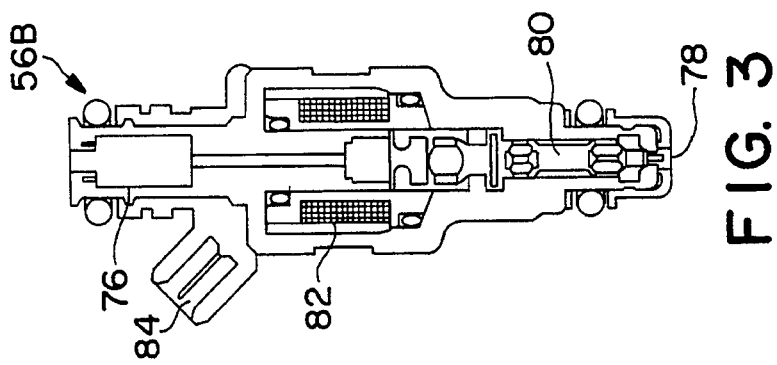
FIG. 3 is a cross section of another type of liquid methoprene injector suitable for use in the invention.

In FIGS. 3 and 4, an electromagnetic injector 56B is illustrated which is also typical of a conventional fuel injector used in the diesel engine art. In the injector 56B, the liquid methoprene is fed from an input pipe 74 past a filter 76 to a discharge nozzle 78 operated under the control of a valve 80. The valve 80, in turn, is controlled by a solenoid coil 82 operated by electric current supplied to a terminal connection 84.

Alternative embodiments of the manifold in which the liquid methoprene is injected into the high pressure steam of the steam tunnel 10 are designated by the reference numerals 38 and 38A in FIGS. 5 and 6, respectively. As shown in FIG. 5, a single liquid methoprene injector 56 is positioned at the upstream end of the manifold 38, preferably at the inlet of steam from the supply conduit 40. In this embodiment, a uniform mixture of methoprene and steam is supplied to all of the outlet conduits 52 from the manifold 38 to the nozzles 36.

In the manifold 38A of FIG. 6, a plurality of methoprene injectors, equal in number to the outlet conduits 52, are oriented to inject methoprene into the steam as it exits through the outlet conduits 52. As such, the liquid methoprene may be injected into the high-pressure steam by individual injectors capable of being independently controlled. Thus, the rate of liquid methoprene injection may be the same for all of the nozzles 36, or, the rate of liquid methoprene injection may be varied for independent steam nozzles 36 along the length of the tunnel 26. In this manner, the liquid methoprene injectors may be varied in dependence on the loosened state of the leaf pads along the length of the tunnel section 26.

As stated above, a general objective in the application of methoprene to tobacco leaves is to arrive at a spread of approximately 5 ppm of methoprene in the packed tobacco product. Because tobacco is metered into the steam tunnel feed hopper 20 at a known rate, the amount of liquid methoprene to be injected into the high pressure steam is easily calculated. For example, if the liquid methoprene is the commercially available Kabat®, the formula for the amount of liquid methoprene to be injected is:

Kabat® (kgs)/Tobacco (kgs)×51250=Methoprene (ppm)

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for applying liquid methoprene to oriental tobacco to inhibit the growth of tobacco beetles, the method comprising the steps of:

subjecting oriental tobacco leaves to kinetic energy of high-pressure dry steam exiting from nozzles against and through the tobacco leaves;

injecting the liquid methoprene into the steam before it exits the nozzles.

2. The method recited in claim 1 wherein the tobacco leaves subjected to the high pressure steam are fed at a constant rate of flow.

3. The method recited in claim 2 wherein the injected liquid methoprene is metered in accordance with the constant rate of flow.

4. Apparatus for applying methoprene to oriental tobacco to inhibit the growth of tobacco beetles, comprising:

a vibrating steam tunnel having steam nozzles for subjecting oriental tobacco leaves to kinetic energy of high-pressure dry steam exiting from the nozzle against and through the tobacco leaves;

a supply of liquid methoprene; and means for injecting the liquid methoprene into the steam upstream from the nozzles.

5. The apparatus recited in claim 4 wherein said means for injecting the liquid methoprene into the steam comprises a manifold having a high pressure steam inlet and a plurality of outlets in fluid communication with the nozzles, respectively, at least one injector in said manifold, and means for supplying liquid methoprene to said at least one injector at pressure greater than steam pressure.

6. The apparatus recited in claim 5, wherein the high pressure steam inlet is located at one end of said manifold, said at least one injector being located near said steam inlet.

7. The apparatus recited in claim 6, wherein said at least one injector is oriented to discharge liquid methoprene in the direction of steam flow though said inlet.

8. The apparatus recited in claim 5, comprising a plurality of injectors in said manifold, one injector for each of said outlets.

9. The apparatus recited in claim 8, wherein each of said plurality of injectors is oriented to discharge liquid methoprene in the direction of steam flow though said outlets.

* * * * *